| United States Patent [19] | [11] 4,032,536 |
| --- | --- |
| Raeymaekers et al. | [45] June 28, 1977 |

[54] (1H-BENZIMIDAZOL-2-YL)CARBAMATES

[75] Inventors: Alfons H. M. Raeymaekers, Beerse; Jozef H. L. Van Gelder, Tielen, both of Belgium

[73] Assignee: Janssen Pharmaceutica N.V., Beerse, Belgium

[22] Filed: July 22, 1976

[21] Appl. No.: 707,750

[52] U.S. Cl. .................. 260/309.2; 260/332.3 H; 260/340.7; 260/340.9

[51] Int. Cl.² ............. C07D 405/08; C07D 405/14

[58] Field of Search ............................. 260/309.2

[56] References Cited

UNITED STATES PATENTS

| 3,657,267 | 4/1972 | Van Gelder et al. | 260/309.2 |
| 3,935,209 | 1/1976 | Beard et al. | 260/309.2 |
| 3,969,526 | 7/1976 | Gyurik et al. | 260/309.2 |

Primary Examiner—Natalie Trousof
Attorney, Agent, or Firm—Salvatore R. Conte

[57] ABSTRACT

Novel (1H-benzimidazol-2-yl)carbamates useful as anthelmintic agents.

7 Claims, No Drawings

(1H-BENZIMIDAZOL-2-YL)CARBAMATES

BACKGROUND OF THE INVENTION

In U.S. Pat. No. 3,657,267 there are described a series of anthelmintic 5-acyl-(1H-benzimidazol-2-yl)carbamates, the best known member of which is methyl(5-benzoyl-1H-benzimidazol-2-yl)carbamate, generically designated as mebendazole. The novel compounds of this invention differ from the foregoing essentially by the nature of the ketal substituent in the 5-position of the benzimidazole nucleus.

DESCRIPTION OF THE PREFERRED EMBODIMENTS

This invention relates to novel chemical compounds and more particularly to a series of (1H-benzimidazol-2-yl)carbamates which are structurally represented by the formula:

(I)

wherein:
R is a member selected from the group consisting of phenyl, halophenyl and 2-thienyl;
$R^1$ is lower alkyl; and
A is an alkylene chain having the formula:

$$-CH- \left[ \begin{array}{c} R^3 \\ | \\ C \\ | \\ R^4 \end{array} \right]_n -CH- \\ \phantom{-}\phantom{CH}R^2 \phantom{aaaa} R^5$$

wherein n is an integer of from 0 to 1 inclusive, and $R^2$, $R^3$, $R^4$ and $R^5$ are each independently selected from the group consisting of hydrogen and lower alkyl.

As used in this and following definitions "lower alkyl" is meant to include straight and branch chained alkyl radicals having from 1 to 5 carbon atoms such as, for example, methyl, ethyl, propyl, butyl, pentyl and the like; and the term "halo" is generic to halogens of atomic weight less than 127, i.e., fluoro, chloro, bromo and iodo.

The compounds of formula (I) are conveniently prepared by subjecting an appropriate 1,2-benzenediamine of formula (II) to a cyclization reaction with an appropriate cyclizing agent as known in the art of preparing (1H-benzimidazol-2-yl)carbamates starting from 1,2-benzenediamines.

(II)

Suitable cyclizing agents which advantageously may be employed include, for example, i. (iminomethoxymethyl)carbamates of formula (III)

$$CH_3-O-\overset{\overset{\displaystyle NH}{\|}}{C}-NH-COO(\text{lower alkyl});\quad\text{(III)}$$

ii. [(lower alkyloxycarbonylamino) (R$^6$-thio)methylene]carbamates of formula (IV)

$$(\text{lower alkyl})-O-\overset{\overset{\displaystyle O}{\|}}{C}-HN-\overset{\overset{\displaystyle S-R^6}{|}}{C}=N-COO(\text{lower alkyl})\quad\text{(IV)}$$

wherein $R^6$ is hydrogen or methyl;

iii. lower alkyl carbonoisothiocyanatidates of formula (V)

$$(\text{lower alkyl})-O-\overset{\overset{\displaystyle O}{\|}}{C}-NCS;\quad\text{(V)}$$

iv. lower alkyl lower alkylcarbamothioates of formula (VI)

$$(\text{lower alkyl})-NH-\overset{\overset{\displaystyle S}{\|}}{C}-O(\text{lower alkyl});\text{ and}\quad\text{(VI)}$$

v. dilower alkyl cyanimidodicarbonates of formula (VII)

$$\left[(\text{lower alkyl})-O-\overset{\overset{\displaystyle O}{\|}}{C}\right]_2 N-CN.\quad\text{(VII)}$$

The foregoing cyclization reactions may all be performed following art-known procedures as described in the literature.

The 1,2-benzenediamines of formula (II), used as starting materials in the preparation of the compounds (I), are prepared as follows:

An appropriate ketone of formula (VIII) wherein R is as previously defined is subjected to a ketalization reaction with an appropriate alkanediol of formula (IX) wherein n, $R^2$, $R^3$, $R^4$ and $R^5$ have the above defined meaning to obtain an intermediate of formula (X). Said ketalization reaction may be carried out in a similar manner to that described for the preparation of 2-bromomethyl-2,4-diphenyl-1,3-diphenyl-1,3-dioxolane [Synthesis, 1974(I), 23]. Preferably the ketalization is performed by stirring and refluxing the reactants together for several hours with azeotropic water removal in an appropriate organic solvent, preferably in the presence of a simple alkanol such as, for example, ethanol, propanol, butanol, pentanol and the like, and in the presence of an appropriate strong acid such as 4-methylbenzenesulfonic acid. Suitable solvents are, for example, aromatic hydrocarbons, such as benzene, methylbenzene, dimethylbenzene and the like and saturated hydrocarbons, such as cyclohexane. The intermediates (II) are then easily derived from (X) by reducing the nitro group of the latter to an amine group following art-known nitro-to-amine reduction procedures such as by the reaction of (X) with nascent hydrogen or by catalytic hydrogenation in the presence of an appropriate catalyst such as, for example, Raney-nickel.

The foregoing reactions are illustrated in the following schematic representation:

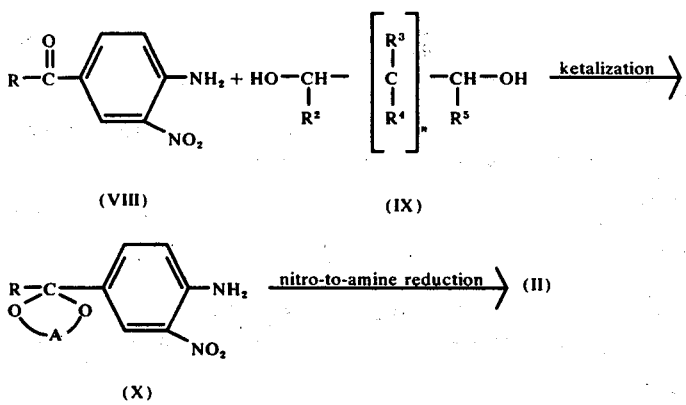

(VIII)　　　　　　　　(IX)

(X)

The benzeneamines of formula (VIII), used as starting materials herein, are generally known and may be prepared following art-known procedures. A number of such compounds and methods of preparing the same are described, for example in U.S. Pat. No. 3,657,267.

Said starting materials may still conveniently be prepared as follows.

Methoxybenzene, (XI) is acylated with an appropriate acylhalide (XII) under classical Friedel-Crafts conditions yielding an intermediate of formula (XIII). The latter is dissolved in an appropriate reaction-inert organic solvent such as dichloromethane, and nitrated with a mixture of nitric acid and sulfuric acid while cooling to about 0° C. The thus obtained (XIV) is then converted into the desired (VIII) by exchanging the methoxy group of the former for an amino group. This amination reaction is preferably carried out by stirring and heating (XIV) with ammonia at elevated pressure in an appropriate solvent such as, for example a mixture of water and an appropriate alkanol such as 2-propanol.

The foregoing reactions are illustrated hereafter.

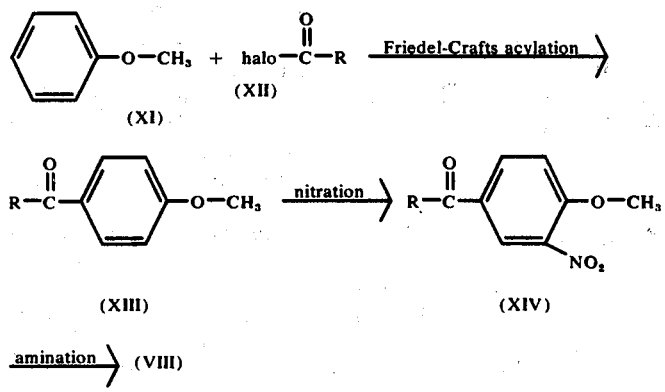

(XI)　　　　　　　　　　　　　　(XIII)　　　　　　　　(XIV)

amination → (VIII)

The (1H-benzimidazol-2-yl)carbamates of formula (I) are potent anthelmintics, and, as such, they are useful agent in the treatment of human beings and animals suffering from various helminth infections of the intestinal tract.

The compounds (I) are active against a broad sprectrum of helminths, e.g., Trichostrongylus, Ostertagia, Cooperia, Haemonchus, Strongyloides, Ascaris, Heterakis, Syphacia and the like. Depending upon the weight of the host, dosages of from about 0.5 to about 40 mg/kg of body weight daily will generally be sufficient to effectively eliminate the infectious organisms. Anthelminthic compositions comprising an effective amount of an active compound (I), either alone or in combination with other active therapeutic ingredients, in admixture with suitable carriers may be readily prepared according to conventional pharmaceutical techniques for the usual routes of administration.

The useful anthelmintic properties of the compounds (I) are clearly illustrated by the results obtained in the following experiments on laboratory animals.

A. Activity against Syphacia muris in rats.

Syphacia muris was selected as a test organism since this organism manifests its relationship with the human oxyuris, Enterobin verminicularis, by its life cycle, by the cyclical period of activity and by laying its eggs in the per-anal zone. For artificial infections, adhesive cellophane tape is used to recover the eggs from the perianal skin and this tape is administered orally to rats. The thus-infected animals are housed in individual cages with food and water ad libitum. The compound to be tested is administered orally by gavage. A sterile saline solution or suspension of the compound is made at various concentrations corresponding to 40, 10, 2.5, 1.25, 0.63, 0.31 and 0.16 mg/kg body weight. Control animals receive the same amount of saline. Five days thereafter the animals are sacrified. Coecum, colon and rectum are isolated and washed on a sieve of mesh 100. Table I gives the $ED_{50}$-values for a number of the compounds of formula (I). The compounds listed therein are not given for the purpose of limiting the invention thereto but only to exemplify the useful anthelmintic properties of all the compounds within the scope of formula (I).

B. Activity against Strongyloides ratti in rats.

Young male Wistar rats, weighing about 100 g are used in this test. Infective larvae of Strongyloides ratti are collected from charcoal cultures, put into a beaker with tapwater and stirred magnetically for counting. The rats are infected subcutaneously with about 1000 larvae, treated on day 7 after infection in the same manner as described in experiment A, and autopsied on day 13. The anterior part of the intestine is divided into two sections, each of 10 cm. length and placed inside out on a wood-applicator. These sections are incubated in physiological saline for 4 hours at 37° C. Worms obtained from the sedimentation of incubation saline are sampled and counted under a dissection microscope. In table I are given $ED_{50}$-values for a number of compounds of formula (I). These $ED_{50}$-values represent the amount of the compound under investigation in mg/kg which reduces the number of worms 50% with respect to the number found in the untreated control animals.

TABLE I

| $R\text{-}C\langle{}^O_O\rangle{}^{\,}_A$ | $ED_{50}$-value in mg/kg orally | |
|---|---|---|
| | Syphacia muris in rats | Strongyloides ratti in rats |
|  | 2.5 | 2.5 |
|  | 1.25 | 0.63 |
|  | 5 | 0.31 |
|  | 2.5 | 0.31 |
|  | 2.5 | 1.25 |
|  | 2.5 | 10 |
|  | 10 | 10 |
|  | 10 | 2.5 |

TABLE I-continued

| $R\text{-}C\langle{}^O_O\rangle{}^{\,}_A$ | $ED_{50}$-value in mg/kg orally | |
|---|---|---|
| | Syphacia muris in rats | Strongyloides ratti in rats |
| 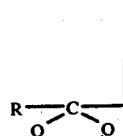 | 40 | 10 |
| 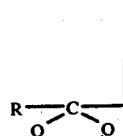 | 10 | 10 |
|  | 40 | 1.25 |

The following examples are intended to illustrate but not to limit, the scope of the present invention. Unless ontherwise stated all parts therein are by weight.

EXAMPLE I

A mixture of 26 parts of (4-amino-3-nitrophenyl)(4-fluorophenyl)methanone, 12 parts of 1,2-ethanediol, 10 parts of 4-methylbenzenesulfonic acid, 32 parts of butanol and 360 parts of benzene is stirred and refluxed for 96 hours with water-separator. Another 5 parts of 4-methylbenzenesulfonic acid are added and stirring at reflux is continued for 72 hours. The reaction mixture is cooled, water is added and the layers are separated. The organic phase is dried, filtered and evaporated. The residue is purified twice by column-chromatography over silica gel using first a mixture of trichloromethane and 2% of methanol and then trichloromethane as eluent. The pure fractions are collected and the eluent is evaporated, yielding 10.1 parts (33.2%) of 4-[2-(4-fluorophenyl)-1,3-dioxolan-2-yl]-2-nitrobenzenamine; mp. 105° C.

EXAMPLE II

Following the procedure of Example I and using equivalent amounts of respectively an appropriate (4-amino-3-nitrophenyl)arylmethanone and an appropriate alkanediol the following ketals are prepared:
2-nitro-4-(2-phenyl-1,3-dioxolan-2-yl)benzenamine; mp. 145° C;
2-nitro-4-[2-(2-thienyl)-1,3-dioxolan-2-yl]benzenamine; mp. 103.5° C;
4-(4-methyl-2-phenyl-1,3-dioxan-2-yl)-2-nitrobenzenamine; mp. 175.8° C;
4-[4-methyl-2-(2-thienyl)-1,3-dioxan-2-yl]-2-nitrobenzenamine as a residue; and
4-[5,5-dimethyl-2-(2-thienyl)-1,3-dioxan-2-yl]-2-nitrobenzenamine; mp. 140° C.

EXAMPLE III

A mixture of 31.5 parts of (4-amino-3-nitrophenyl)-phenylmethanone, 21 parts of 2,2-dimethyl-1,3-propanediol, 2 parts of 4-methylbenzenesulfonic acid, 40 parts of butanol and 450 parts of methylbenzene is stirred and refluxed for 16 hours with water-separator. The reaction mixture is cooled and washed with ammonium hydroxide. The organic phase is dried, filtered and evaporated. The residue is crystallized from 2,2'-oxybispropane, yielding 27.5 parts (55%) of 4-(5,5-dimethyl-2-phenyl-1,3-dioxan-2-yl)-2-nitrobenzenamine; mp. 139.8° C.

EXAMPLE IV

Following the procedure of Example III and using equivalent amounts of the appropriate starting materials there are prepared:
4-[4-methyl-2-(2-thienyl)-1,3-dioxolan-2-yl]-2-nitrobenzenamine; mp. 117° C; and
4-(4,5-dimethyl-2-phenyl-1,3-dioxolan-2-yl)-2-nitrobenzenamine; mp. 133.8° C.

EXAMPLE V

A solution of 31.5 parts of (4-amino-3-nitrophenyl)-phenylmethanone, 15.2 parts of 1,2-propanediol and 5 parts of 4-methylbenzenesulfonic acid in 40 parts of butanol and 450 parts of methylbenzene is stirred and refluxed for 17 hours. The reaction mixture is cooled and 90 parts of ammonium hydroxide are added (to remove the 4-methylbenzenesulfonic acid). The organic phase is separated, washed with water, dried, filtered and evaporated. The residue is crystallized from methylbenzene. The product is filtered off (the filtrate is set aside), yielding a first fraction of 13.8 parts of 4-(4-methyl-2-phenyl-1,3-dioxolan-2-yl)-2-nitrobenzenamine; mp. 155.2° C. The filtrate, which was set aside, is evaporated. The residue is purified by column-chromatography over silica gel using a mixture of trichloromethane, methanol and hexane (88:2:10 by volume) as eluent. The pure fractions are collected and the eluent is evaporated, yielding a second fraction of 3.6 parts of 4-(4-methyl-2-phenyl-1,3-dioxolan-2-yl)-2-nitrobenzenamine.

EXAMPLE VI

Following the procedure of Example V there is prepared 4-[4,5-dimethyl-2-(2 -thienyl)-1,3-dioxolan-2-yl]-2-nitrobenzenamine; mp. 120.7° C; by the reaction of (4-amino-3-nitrophenyl)(2-thienyl)methanone with 2,3-butanediol.

EXAMPLE VII

A mixture of 5.04 parts of 4-[5,5-dimethyl-2-(2-thienyl)-1,3-dioxan-2-yl]-2-nitrobenzenamine and 120 parts of methanol is hydrogenated at normal pressure and at room temperature with 3 parts of Raney-nickel catalyst. After the calculated amount of hydrogen is taken up, the catalyst is filtered off and the filtrate is evaporated, yielding 4.5 parts (100%) of 4-[5,5-dimethyl-2-(2-thienyl)-1,3-dioxan-2-yl]-1,2-benzenediamine; mp. 178° C.

EXAMPLE VIII

Following the procedure of Example VII and using an equivalent amount of an appropriate 2-nitrobenzenamine as a starting material, the following benzenediamines are obtained as a residue:

4-[2-(4-fluorophenyl)-1,3-dioxolan-2-yl]-1,2-benzenediamine;
4-(2-phenyl-1,3-dioxolan-2-yl)-1,2-benzenediamine;
4-(4-methyl-2-phenyl-1,3-dioxolan-2-yl)-1,2-benzenediamine;
4-(4,5-dimethyl-2-phenyl-1,3-dioxolan-2-yl)-1,2-benzenediamine;
4-(4-methyl-2-phenyl-1,3-dioxan-2-yl)-1,2-benzenediamine;
4-(5,5-dimethyl-2-phenyl-1,3-dioxan-2-yl)-1,2-benzenediamine;
4-[2-(2-thienyl)-1,3-dioxolan-2-yl]-1,2-benzenediamine; 4-[4-methyl-2-(2-thienyl)-1,3-dioxolan-2-yl]-1,2-benzenediamine;
4-[4,5-dimethyl-2-(2-thienyl)-1,3-dioxolan-2-yl]-1,2-benzenediamine; and
4-[4-methyl-2-(2-thienyl)-1,3-dioxan-2-yl]-1,2-benzenediamine.

EXAMPLE IX

A mixture of 5.5 parts of 4-[4-(4-fluorophenyl)-1,3-dioxolan2-yl]-1,2-benzenediamine, 6.2 parts of methyl [(methoxycarbonylamino)(methylthio)methylene]carbamate, 4.8 parts of acetic acid and 225 parts of trichloromethane is stirred and refluxed for 17 hours. The reaction mixture is evaporated in vacuo. The residue is triturated in methanol. The product is filtered off, washed with 2,2' -oxybispropane and dried, yielding 3 parts (42%) of methyl {5-[2-(4-fluorophenyl)-1,3-dioxolan-2-yl]-1H-benzimidazol-2-yl}carbamate; mp. 227.7° C.

EXAMPLE X

Following the procedure of Example IX and using an equivalent amount of an appropriate benzenediamine in place of the 4-[2-(4-fluorophenyl)-1,3-dioxolan-2-yl]-1,2-benzenediamine used therein the following compounds are prepared:
methyl [5-(2-phenyl-1,3-dioxolan-2-yl)-1H-benzimidazol-2-yl]carbamate; mp. 270.4° C;
methyl [5-(4-methyl-2-phenyl-1,3-dioxolan-2-yl)-1H-benzimidazol-2-yl]carbamate; mp. 289.6° C;
methyl [5-(4,5-dimethyl-2-phenyl-1,3-dioxolan-2-yl)-1H-benzimidazol-2-yl]crbamate; mp. 270° C;
methyl [5-(4-methyl-2-phenyl-1,3-dioxan-2-yl)-1H-benzimidazol-2-yl]crbamate; mp. 202.5° C;
methyl {5-[2-(2-thienyl)-1,3-dioxolan-2-yl]-1H-benzimidazol-2-yl}carbamate; mp. 263° C (dec.);
methyl {5-[4-methyl-2-(2-thienyl)-1,3-dioxolan-2-yl]-1H-benzimidazol2-yl}carbamate; mp. 211.7° C;
methyl {5-[4,5-dimethyl-2-(2-thienyl)-1,3-dioxolan-2-yl]-1H-benzimidazol-2-yl}carbamate; mp. 221.8° C;
methyl {5-[4-methyl-2-(2-thienyl)-1,3-dioxan-2-yl]-1H-benzimidazol-2-yl}carbamate. hemihydrate; mp. 162° C; and
methyl {5-[5,5-dimethyl-2-(2-thienyl)-1,3-dioxan-2-yl]-1-benzimidazol-2-yl}carbamate; mp. 235.2°–235.9° C.

EXAMPLE XI

A solution of 6 parts of 4-(5,5-dimethyl-2-phenyl-1,3-dioxan-2yl)-1,2-benzenediamine, 4.95 parts of methyl [(methylcarbonylamino)(methylthio)methylene[carbamate and 5 parts of acetic acid in 300 parts of trichloromethane is stirred and refluxed for 24 hours. The reaction mixture is evaporated and the residue is purified by column-chromatography over silica gel using a mixture of trichloromethane and 5% of methanol as eluent. The pure fractions are collected and the eluent is evaporated, yielding 3.7 parts (48.5%) of methyl [5-(5,5-dimethyl-2-phenyl-1,3-dioxan-2-yl)-1H-benzimidazol-2-yl]carbamate; mp. 224.5° C.

EXAMPLE XII

Following the procedure of Example IX and using equivalent amounts of the appropriate starting materials, the following compounds of formula I are prepared.

Ethyl {5-[2-(4-fluorophenyl)-1,3-dioxolan-2-yl]-H-benzimidazol-2-yl}carbamate;

Propyl {5-[2-(4-fluorophenyl)-1,3-dioxolan-2-yl]-1H-benzimidazol-2-yl}carbamate;

Ethyl [5-(2-phenyl-1,3-dioxolan-2-yl)-1H-benzimidazol-2-yl]carbamate;

Butyl [5-(2-phenyl-1,3-dioxolan-2-yl)-1H-benzimidazol-2-yl]carbamate;

Ethyl [5-(4-methyl-2-phenyl-1,3-dioxolan-2-yl)-1H-benzimidazol-2-yl]carbamate;

Ethyl [5-(4,5-dimethyl-2-phenyl-1,3-dioxolan-2-yl)-1H-benzimidazol-2-yl]carbamate;

2-Propyl [5-(4,5-dimethyl-2-phenyl-1,3-dioxolan-2-yl)-1H-benzimidazol-2-yl]carbamate;

Ethyl [5-(4-methyl-2-phenyl-1,3-dioxan-2-yl)-1H-benzimidazol-2-yl]carbamate; and Ethyl {5-[2-thienyl)-1,3-dioxolan-2-yl]-1H-benzimidazol-2-yl}carbamate.

We claim:

1. A (1H-benzimidazol-2-yl)carbamate of the formula:

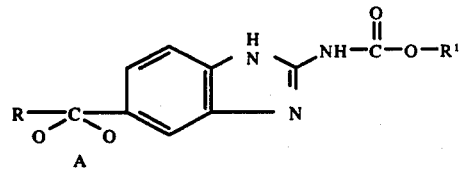

wherein:

R is a member selected from the group consisting of phenyl, halophenyl and 2-thienyl;

$R^1$ is lower alkyl; and

A is an alkylene chain having the formula:

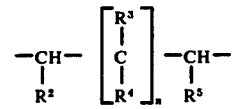

wherein $n$ is in integer of from 0 to 1 inclusive, and $R^2$, $R^3$, $R^4$ and $R^5$ are each independently selected from the group consisting of hydrogen and lower alkyl.

2. Methyl {5-[2-(4-fluorophenyl)-1,3-dioxolan-2-yl]-1H-benzimidazol-2-yl}carbamate.

3. Methyl [5-(2-phenyl-1,3-dioxolan-2-yl)-1H-benzimidazol-2-yl]carbamate.

4. Methyl [5-(4-methyl-2-phenyl-1,3-dioxolan-2-yl)-1H-benzimidazol-2-yl]carbamate.

5. Methyl [5-(4,5-dimethyl-2-phenyl-1,3-dioxolan-2-yl)-1H-benzimidazol-2-yl]carbamate.

6. Methyl {5-[2-(2-thienyl)-1,3-dioxolan-2-yl]-1H-benzimidazol-2-yl}carbamate.

7. Methyl [5-(4-methyl-2-phenyl-1,3-dioxan-2-yl)-1H-benzimidazol-2yl]carbamate.

* * * * *

UNITED STATES PATENT AND TRADEMARK OFFICE
CERTIFICATE OF CORRECTION

PATENT NO. : 4,032,536
DATED : June 28, 1977
INVENTOR(S) : Alfons H.M. Raeymaekers et al.

It is certified that error appears in the above-identified patent and that said Letters Patent are hereby corrected as shown below:

In Column 8, line 21, "4-[4-fluorophenyl)" should read --- 4-[2-(4-fluorophenyl) ---.

In Column 10, line 5, Claim 1, the formula " $\overset{C}{O\diagdown O}$ " $\overset{}{A}$ should read --- $\overset{C}{O\diagdown O}_{A}$ ---.

Signed and Sealed this

Thirtieth Day of May 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,032,536
DATED : June 28, 1977
INVENTOR(S) : Alfons H.M. Raeymaekers & Jozef H.L. Van Gelder It is certified that error appears in the above-identified patent and that said Letters Patent are hereby corrected as shown below:

Col. 8, line 21, "4-[4-fluorophenyl)" sbuld read 4-[2-(4-fluorophenyl)".
Col. 8, line 44, "crbamate" should be "carbamate".
Col. 8, line 46, "crbamate" should be "carbamate".
Col. 8, line 57, "-1-benzimidazol" should read "1H-benzimidazol".
Col. 8, line 64, The bracket is facing the wrong way.
Col. 9, line 12, "-H-benzimidazol" should "-1H-benzimidazol".
Col. 9, line 32, "[2-thienyl)" should read "[2-(2-thienyl)".

Col. 10, line 21, "is in" should read "is an".

Signed and Sealed this

Fourth Day of December 1979

[SEAL]

Attest:

SIDNEY A. DIAMOND

Attesting Officer

Commissioner of Patents and Trademarks